(12) United States Patent
Li et al.

(10) Patent No.: US 11,925,440 B2
(45) Date of Patent: Mar. 12, 2024

(54) SMART HEALTH DEVICE ABLE TO MONITOR PHYSIOLOGICAL STATES OF HUMAN BODY

(71) Applicant: Jiangyu Kangjian Innovation Medical Technology(Chengdu) Co., Ltd, Chengdu (CN)

(72) Inventors: Yu-Chao Li, Shenzhen (CN); Lien-Yu Lin, New Taipei (TW); Ying-Wei Sheng, New Taipei (TW); Chieh Kuo, New Taipei (TW); Ping-Hao Liu, New Taipei (TW)

(73) Assignee: Jiangyu Kangjian Innovation Medical Technology(Chengdu) Co., Ltd, Chengdu (CN)

( * ) Notice: Subject to any disclaimer, the term of this patent is extended or adjusted under 35 U.S.C. 154(b) by 153 days.

(21) Appl. No.: 16/906,455

(22) Filed: Jun. 19, 2020

(65) Prior Publication Data
US 2021/0378525 A1 Dec. 9, 2021

(30) Foreign Application Priority Data

Jun. 9, 2020 (CN) .......................... 202010519818.X

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0077* (2013.01); *A61B 5/14532* (2013.01);
(Continued)

(58) Field of Classification Search
CPC .............. A61B 5/02055; A61B 5/0077; A61B 5/14532; A61B 5/14546; A61B 5/7465;
(Continued)

(56) References Cited

U.S. PATENT DOCUMENTS

| | | | | |
|---|---|---|---|---|
| 2007/0167845 A1* | 7/2007 | Sasagawa | .............. | A61B 5/022 600/490 |
| 2012/0252543 A1* | 10/2012 | Cho | ..................... | F16M 13/022 455/575.8 |
| 2012/0295667 A1* | 11/2012 | Tomasini | ................. | H04M 1/04 29/592.1 |

(Continued)

FOREIGN PATENT DOCUMENTS

| | | | | |
|---|---|---|---|---|
| CN | 1128648 A | * | 8/1996 | ......... A61B 5/02141 |
| CN | 206117750 U | * | 4/2017 | |

(Continued)

*Primary Examiner* — Eric J Messersmith
(74) *Attorney, Agent, or Firm* — ScienBiziP, P.C.

(57) ABSTRACT

A single smart health device able to monitor all physiological aspects of a human body includes a body fluid detection module, a temperature detection module, an electrocardiogram detection module, and a control module. The body fluid detection module tests and detects amounts of biological substances in body fluids. The temperature detection module detects a temperature of the human body. The electrocardiogram detection module detects a heart rate of the human body. The control module is electrically connected to the body fluid detection module, the temperature detection module, and the electrocardiogram detection module, and obtains the detected amounts of biological substances, the detected temperature, and the detected heart rate.

10 Claims, 7 Drawing Sheets

(51) Int. Cl.
  *A61B 5/145* (2006.01)
  *A61B 5/022* (2006.01)
  *A61B 5/0245* (2006.01)

(52) U.S. Cl.
  CPC ........ *A61B 5/14546* (2013.01); *A61B 5/7465* (2013.01); *A61B 5/02233* (2013.01); *A61B 5/0245* (2013.01); *A61B 2560/045* (2013.01); *A61B 2562/0295* (2013.01)

(58) Field of Classification Search
  CPC .............. A61B 5/02233; A61B 5/0245; A61B 2560/045; A61B 2560/0295; A61B 5/01; A61B 5/6898; H04M 1/04; H04M 1/21; H04M 1/72454; H04M 1/026; H04M 1/18; H04M 2250/12; H04M 2250/22; G01N 33/50
  See application file for complete search history.

(56) References Cited

U.S. PATENT DOCUMENTS

2013/0235546 A1* 9/2013 Sedillo .................... G06F 1/163
                                                            361/809
2017/0345536 A1* 11/2017 Breiwa ................ H01F 7/0247

FOREIGN PATENT DOCUMENTS

| CN | 206117750 U | | 4/2017 | |
|----|----|----|----|----|
| CN | 206422805 U | * | 8/2017 | |
| CN | 206422805 U | | 8/2017 | |
| CN | 108714024 A | * | 10/2018 | ............... A61B 5/01 |
| CN | 208739184 U | * | 4/2019 | |
| CN | 110141221 A | * | 8/2019 | ............... A61B 5/01 |
| JP | 2003299626 A | * | 10/2003 | ......... A61B 5/02141 |
| JP | 2007136075 A | * | 6/2007 | ......... A61B 5/02233 |
| TW | 200616419 A | | 5/2006 | |
| WO | WO-2017173434 A1 | * | 10/2017 | ............... A61B 5/00 |

* cited by examiner

SMART HEALTH DEVICE ABLE TO MONITOR PHYSIOLOGICAL STATES OF HUMAN BODY

FIELD

The subject matter relates to electronic devices, and more particularly, to a smart health device.

BACKGROUND

Portable home-care devices can be used to monitor various physiological processes of human bodies, thereby determining the health status of the human bodies by comparing the readings of processes against standard parameters. The physiological states or processes may include blood pressure, blood sugar, uric acid, cholesterol, electrocardiogram waveform, and temperature of the human body.

However, different physiological processes may be monitored and recorded by a collection of different portable devices. A user may need various portable devices to fully monitor the health status. Therefore, there is room for improvement in the art.

BRIEF DESCRIPTION OF THE DRAWINGS

Implementations of the present technology will now be described, by way of example only, with reference to the attached figures.

DETAILED DESCRIPTION

Figure 1:
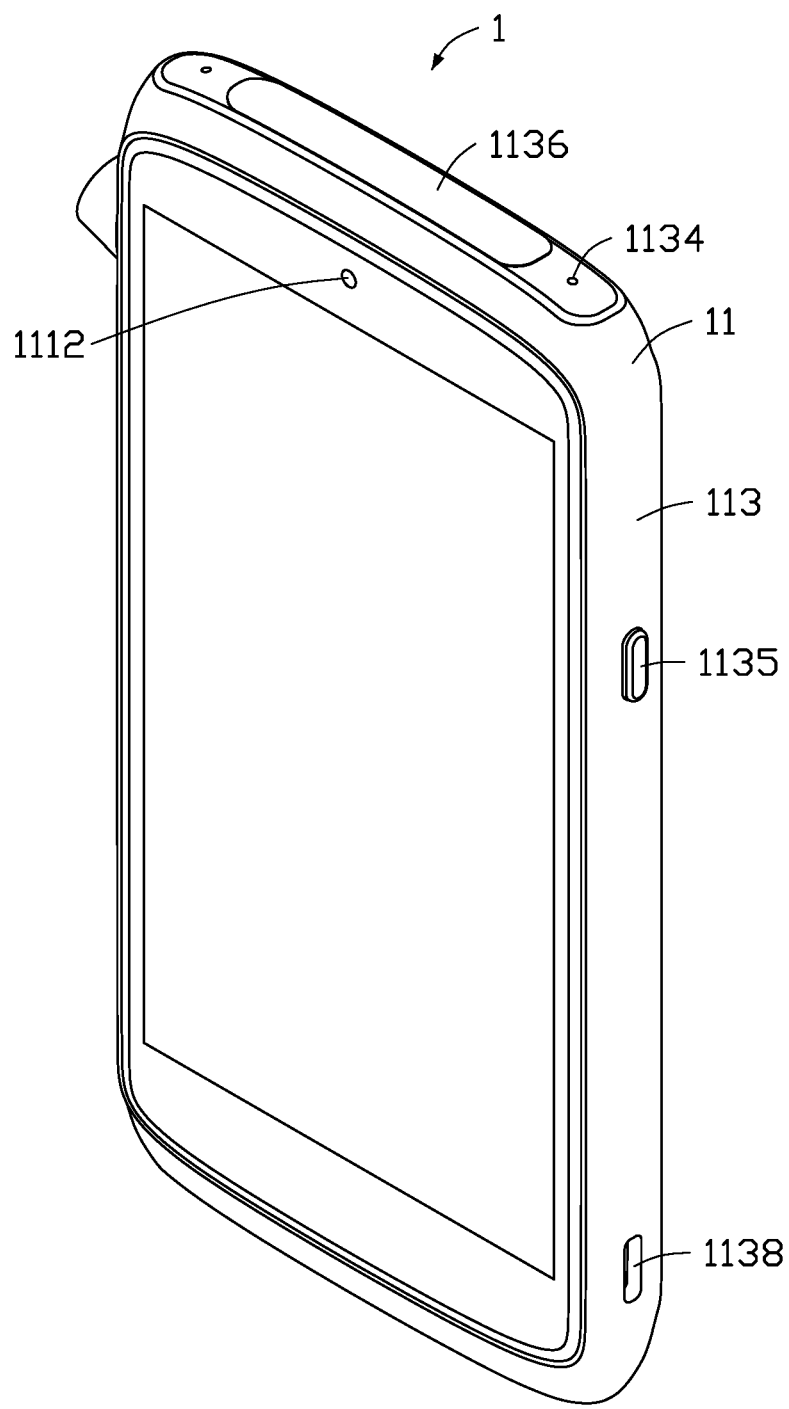
FIG. 1 is a diagrammatic view of a smart health device according to an embodiment of the present disclosure.

It will be appreciated that for simplicity and clarity of illustration, where appropriate, reference numerals have been repeated among the different figures to indicate corresponding or analogous components. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

Figure 2:
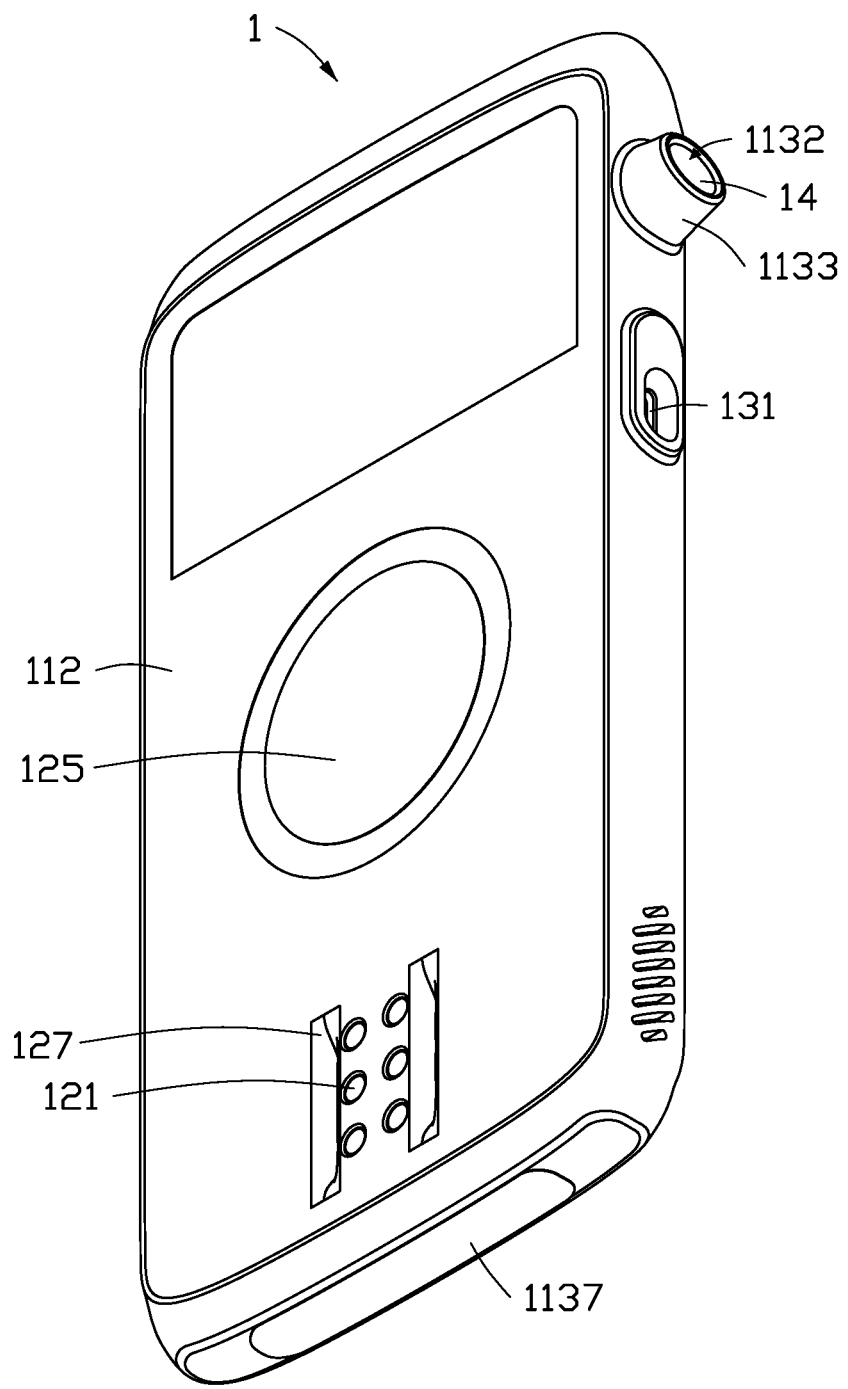
FIG. 2 is similar to FIG. 1, but showing the smart health device from another angle.
Figure 3:
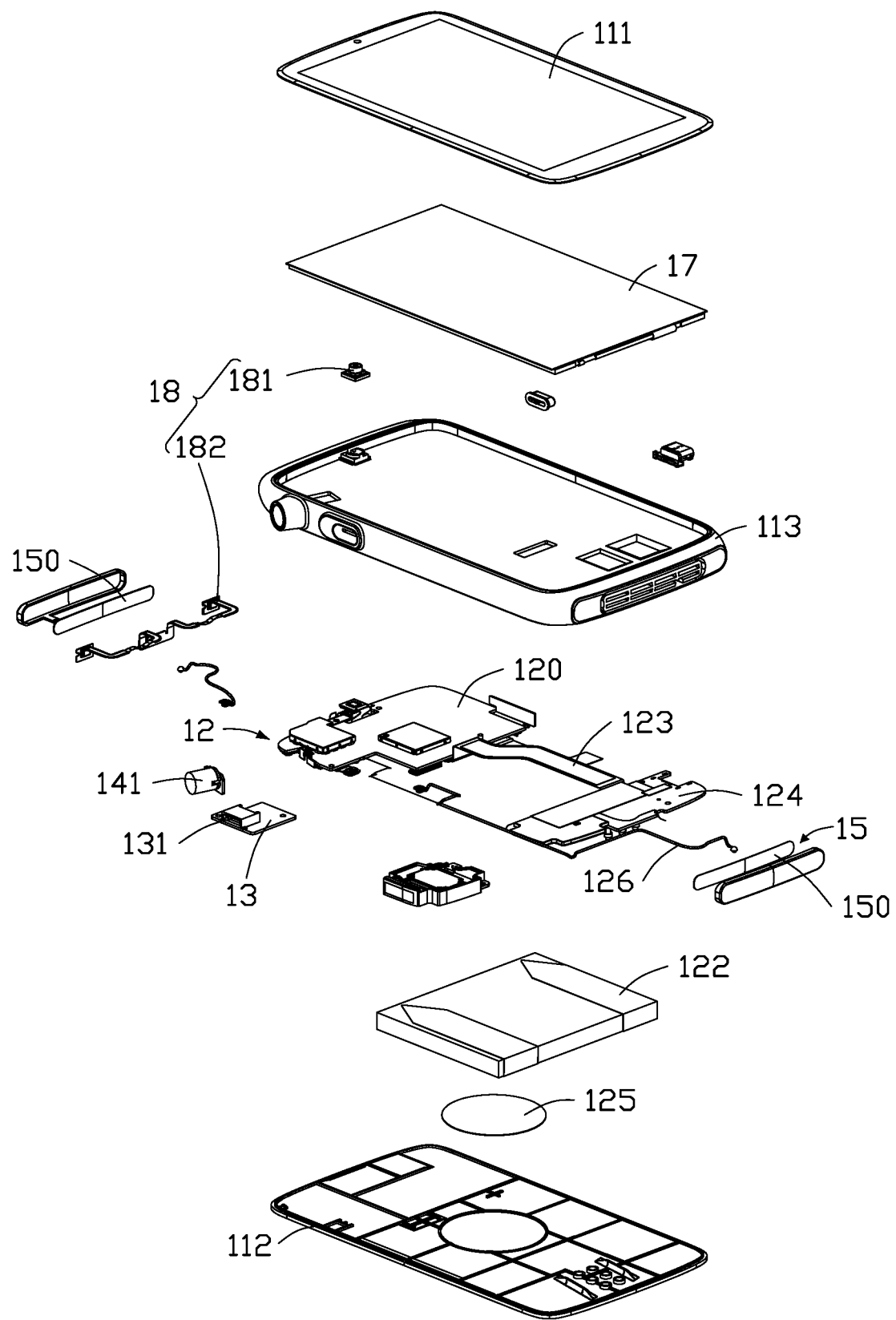
FIG. 3 is an exploded view of the smart health device of FIG. 1.

FIGS. 1 to 3 illustrate an embodiment of a smart health device 1, which includes a casing 11, a control module 12, a body fluid detection module 13, a temperature detection module 14, an electrocardiogram detection module 15, a touch display module 17, and a video module 18. The body fluid detection module 13, the temperature detection module 14, the electrocardiogram detection module 15, the touch display module 17, and the video module 18 are electrically connected to the control module 12. The smart health device 1 may be a smart phone or a table computer, which has a function of detecting various kinds of physiological states and processes of a human body.

The casing 11 includes a side frame 113 and a back plate 112 surrounding edges of the side frame 113. The smart health device 1 further includes a first panel 111. The side frame 113 is connected between the first panel 111 and the back plate 112. The touch display module 17 is disposed under the first panel 111. The touch display module 17 can be used to display information, and the user can also perform touch operations on the touch display module 17 through the first panel 111. In an embodiment, the touch display module 17 may include a display module and a touch module. The display module may be LCD, LED, OLED, QLED, or Micro-LED. The touch module can be self-capacitive or mutual-capacitive touch module. The display module and the touch module may also be integrated together.

The first panel 111 defines a lens hole 1112. The video module 18 includes a camera 181 and a microphone 182. In one embodiment, the camera 181 is disposed in the casing 11 and exposed from the lens hole 1112. The camera 181 captures images or videos through the lens hole 1112. Furthermore, the side frame 113 defines a microphone hole 1134. The microphone 182 is disposed in the casing 11 and exposed from the microphone hole 1134. The microphone 182 receives voice signals from the user. Thus, the user can communicate with an online doctor or a family member through the video module 18.

The side frame 113 further includes a protrusion 1133, a power button 1135, and a charging interface 1138. The protrusion 1133 is disposed at a side of the side frame 113. The protrusion 1133 is hollow and defines a first opening 1132. The temperature detection module 14 is received in the first opening 1132. The power button 1135 and the charging interface 1138 are disposed at a side of the side frame 113 opposite to the protrusion 1133. The power button 1135 controls the smart health device 1 to be on or off. The charging interface 1138 can connect the smart health device 1 to an external device (not shown), to allow the external device to supply electric power to the smart health device 1.

The body fluid detection module 13 detects amounts of biological substances in the body fluid. The biological substances may be related to at least one of health indicators such as blood glucose, cholesterol, and uric acid. The side frame 113 further defines a second opening 131. The body fluid detection module 13 includes a detection sheet 130 disposed in the second opening 131. A test paper carrying a body fluid to be tested can be disposed in the second opening 131. Then, the detection sheet 130 contacts the body fluid, collects the biological substances in the body fluid, and then detects the amounts of the biological substances.

The temperature detection module 14 detects a temperature of the human body. The temperature detection module 14 includes a temperature sensing probe 141. The temperature sensing probe 141 is disposed in the protrusion 1133 and exposed from the first opening 1132. The temperature sensing probe 141 may be an infrared temperature sensor.

The side frame 113 further includes a first electrocardiogram area 1136 and a second electrocardiogram area 1137. The first electrocardiogram area 1136 and the second electrocardiogram area 1137 are respectively disposed at two opposite sides of the side frame 113. The electrocardiogram detection module 15 is disposed in the casing 11 and faces the first electrocardiogram area 1136 and the second electrocardiogram area 1137. The first electrocardiogram area 1136 and the second electrocardiogram area 1137 enable the electrocardiogram detection module 15 to interact with the human body through photoelectric signals. The electrocardiogram detection module 15 detects an electrocardiogram of the human body. In one embodiment, the electrocardiogram detection module 15 includes at least two electrocardiogram probes 150 disposed in the casing 11, and the electrocardiogram probes 150 face the first electrocardiogram area 1136 and the second electrocardiogram area 1137.

Referring to FIG. 3, the control module 12 is disposed in the casing 11. The control module 12 includes a first control board 120, a number of conductive terminals 121, a battery 122, a cable 123, and an auxiliary control board 124, and a data transmission interface 126. The body fluid detection module 13, the temperature detection module 14, the electrocardiogram detection module 15, the touch display module 17, and the video module 18 are electrically connected to the first control board 120. Thus, the first control board 120 can obtain the readings from the body fluid detection module 13, the temperature detection module 14, and the electrocardiogram detection module 15, that is, the detected amounts of the biological substances, the detected temperature, and the detected electrocardiogram. Then, the touch display module 17 can display the readings obtained by the first control board 120. In an embodiment, each of the first control board 120 and the auxiliary control board 124 may be a printed circuit board, a flexible circuit board, or a rigid-flexible circuit board. The battery 122 supplies electric power to other electronic components of the smart health device 1. The conductive terminals 121 are exposed from the back plate 112. The cable 123 and the auxiliary control board 124 cooperate with the first control board 120 to perform the control. The data transmission interface 126 may include at least one of BLUETOOTH interface, WIFI interface, or infrared interface.

Figure 4:
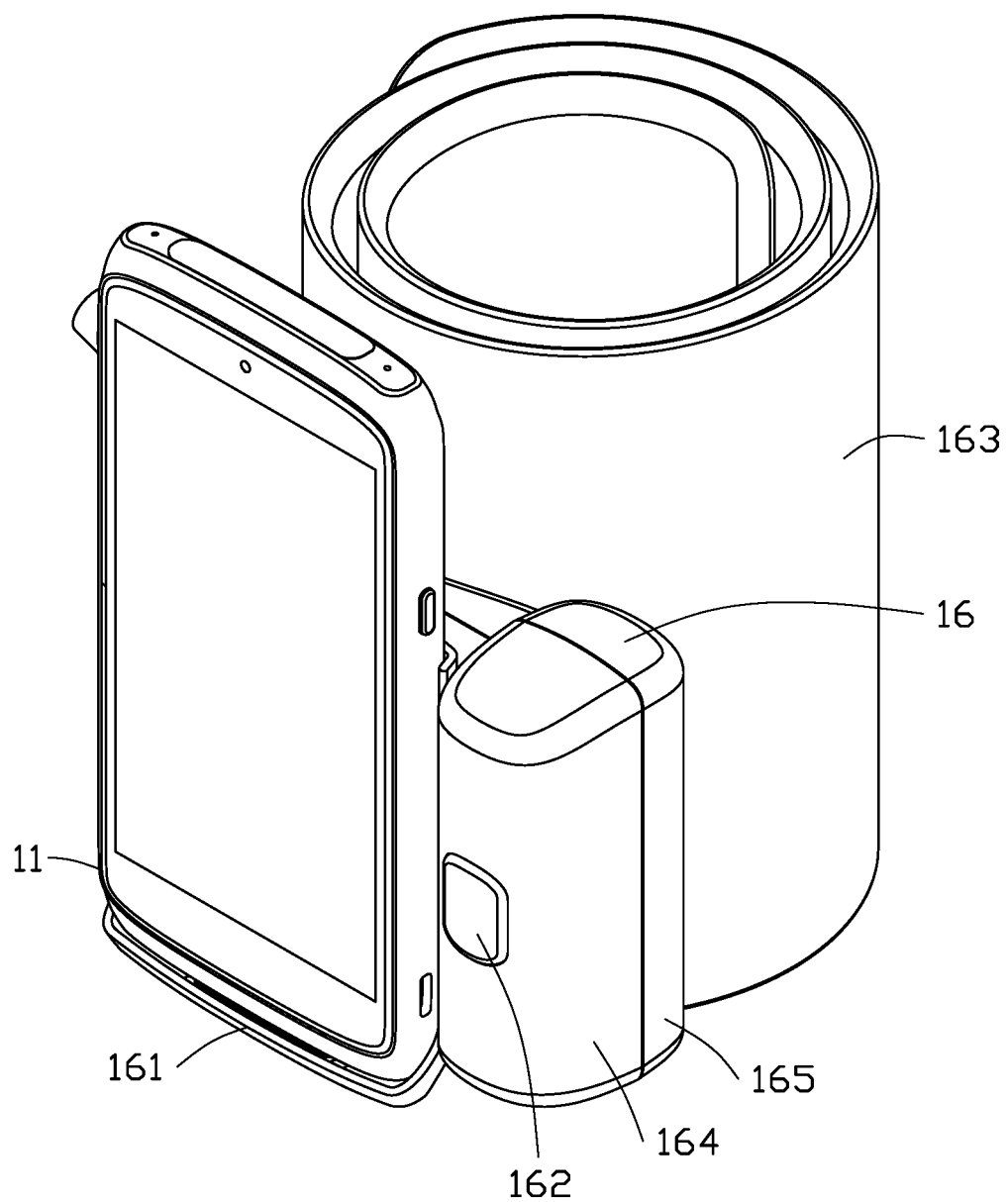
FIG. 4 is a diagrammatic view of a smart health device according to another embodiment of the present disclosure.
Figure 5:
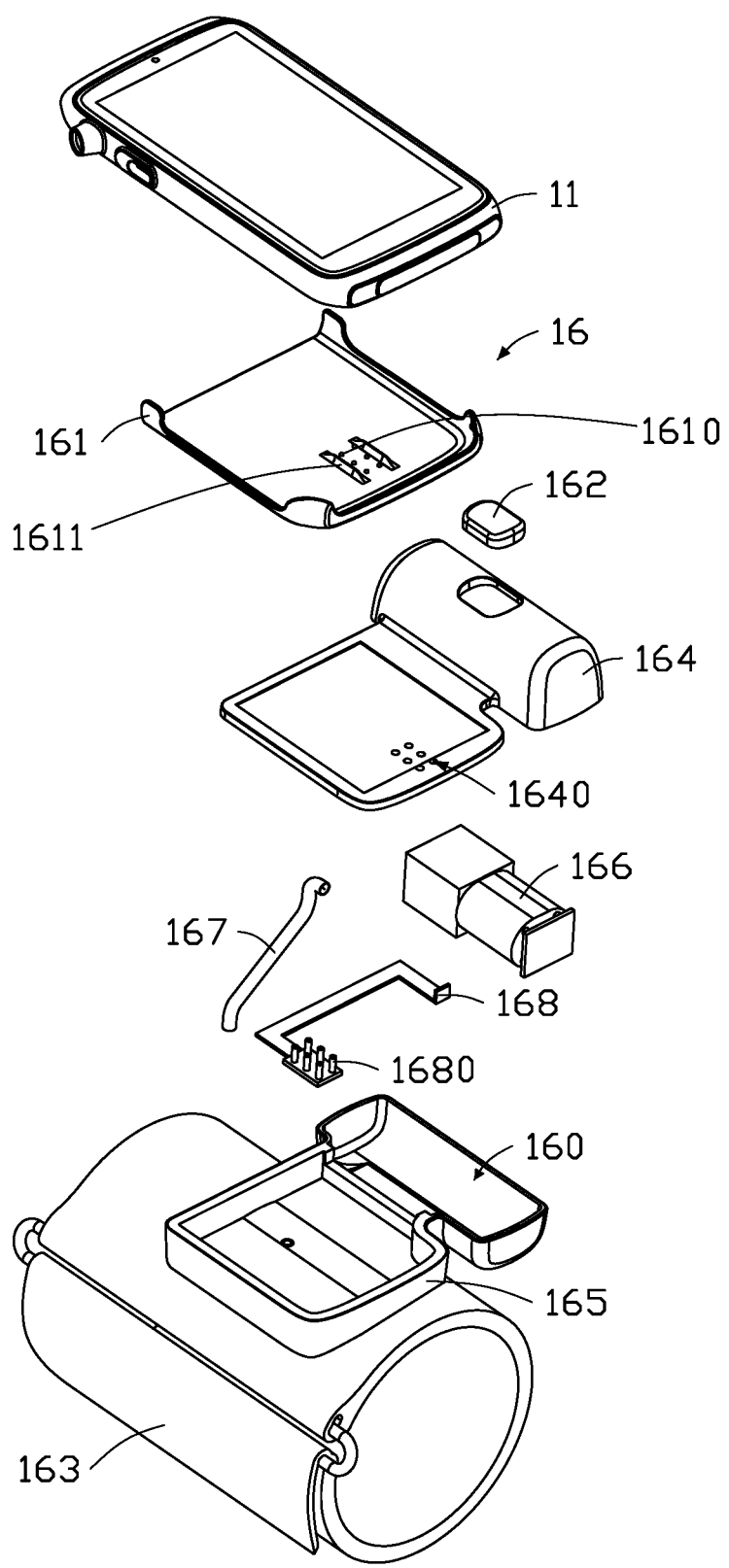
FIG. 5 is an exploded view of the smart health device of FIG. 4.

Referring to FIGS. 4 to 5, in another embodiment, the smart health device 1 further includes a blood pressure detection module 16. The blood pressure detection module 16 is detachably connected to the back plate 112. The blood pressure detection module 16 includes a holding plate 161, a switch 162, an armband 163, an upper cover 164, a lower cover 165, an air pump assembly 166, an air tube 167, and a second control board 168. The casing 11 is movably connected to the holding plate 161. The upper cover 164 is connected to the holding plate 161. The lower cover 165 is connected to the upper cover 164. The upper cover 164 and the lower cover 165 cooperatively define a receiving cavity 160 for receiving the air pump assembly 166, the air tube 167, and the second control board 168. The armband 163 is connected to the lower cover 165, and detects a blood pressure of the human body. The second control board 168 is electrically connected to the armband 163 to obtain the detected blood pressure. The air tube 167 is connected to the air pump assembly 166 and the armband 163. The air pump assembly 166 charges or discharges air from the armband 163. The switch 162 is exposed from the upper cover 164, and electrically connected to the air pump assembly 166. The switch 162 controls the blood pressure detection module 16 to be on or off through the air pump assembly 166. The upper cover 164 defines a plurality of first through holes 1640. The holding plate 161 defines a plurality of second through holes 1610 corresponding to the first through holes 1640. The second control board 168 includes a plurality of conductive pins 1680. The conductive pins 1680 passes through the first through holes 1640 and the second through holes 1610, and then are electrically connected to the conductive terminals 121. The second connection end 169 is electrically connected to the second control board 168. When the casing 11 is supported by the holding plate 161, the conductive terminals 121 are electrically connected to the conductive pins 1680, thereby electrically connecting the second control board 168 and the control module 12 together. Thus, the first control board 120 can further obtain the detected blood pressure from the second control board 168.

Referring to FIGS. 2 and 5, in one embodiment, the back plate 112 further defines two slots 127 disposed at opposite sides of the conductive terminals 121. The holding plate 161 further includes two protruding blocks 1611 disposed at opposite sides of the second through holes 1610. When the casing 11 is supported by the holding plate 161, the protruding blocks 1611 are received in the slots 127, thereby positioning the conductive pins 1680 to the conductive terminals 121. That is, the conductive pins 1680 are prevented from contacting other areas of the back plate 112, and damages to the conductive pins 1680 are thus avoided.

Figure 6:
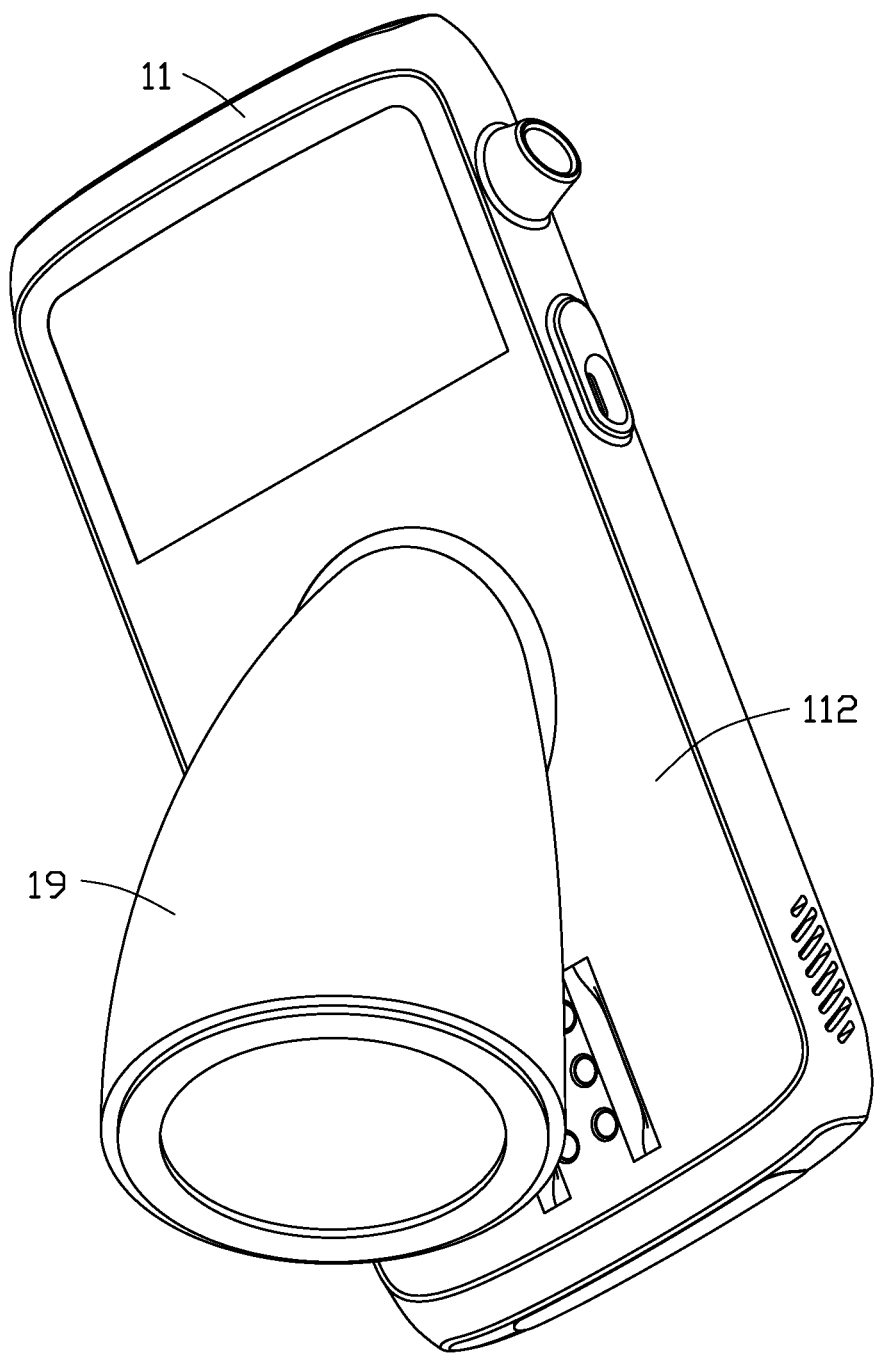
FIG. 6 is a diagrammatic view of a smart health device according to yet another embodiment of the present disclosure.
Figure 7:
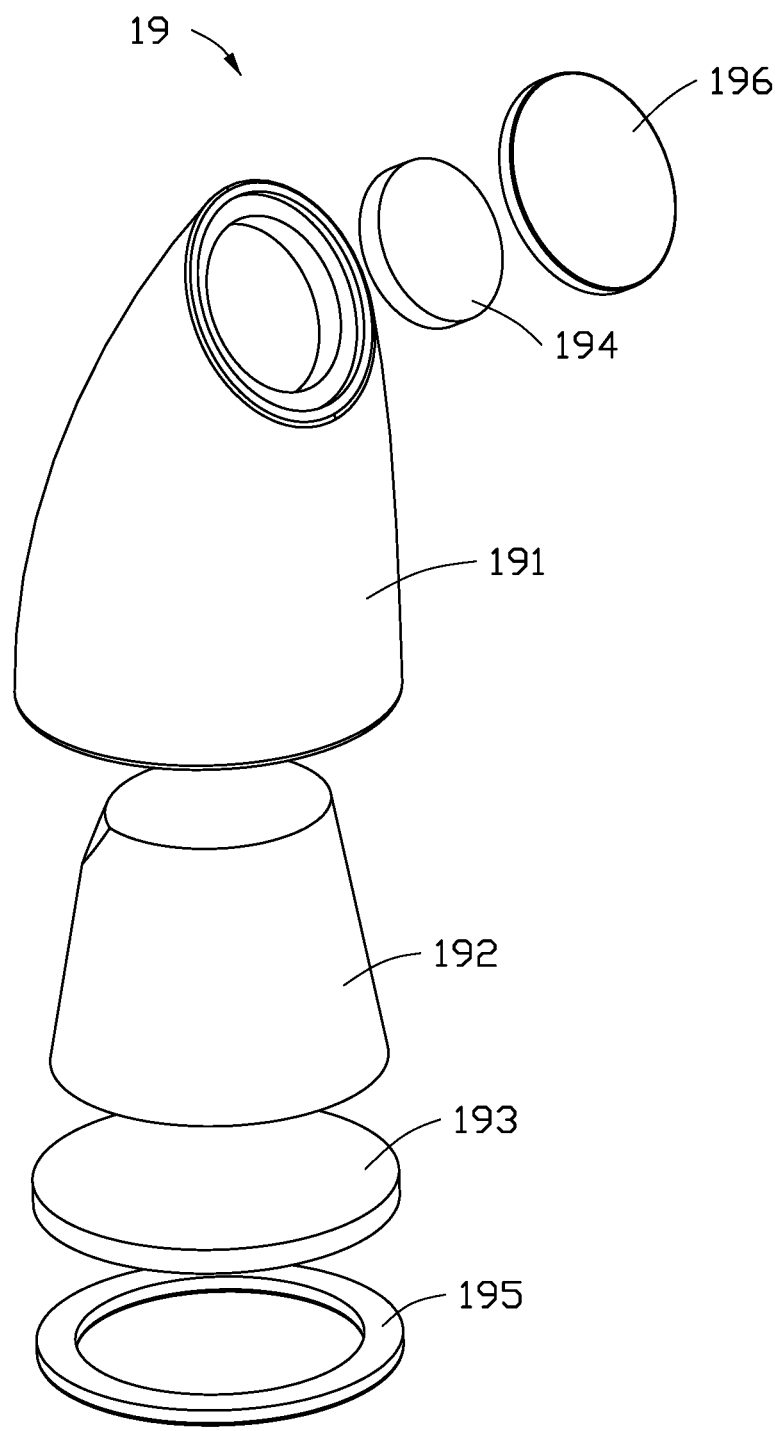
FIG. 7 is a diagrammatic view of a support assembly of the smart health device of FIG. 6.

Referring to FIGS. 6 to 7, in yet another embodiment, the smart health device 1 further includes a support assembly 19. The support assembly 19 is detachably connected to the back plate 112. The support assembly 19 includes a support shell 191, a counterweight block 192, a support cover 193, a magnet 194, a first rubber pad 195, and a second rubber pad 196. The support assembly 19 is movably connected to the back plate 112. In an embodiment, the support shell 191 is hollow, and the counterweight block 192 is disposed in the support shell 191. The first rubber pad 195 and the second rubber pad 196 are disposed at opposite ends of the support shell 191. The support cover 193 is connected to the first rubber pad 195 and supports the counterweight block 192. The magnet 194 is connected to the second rubber pad 196 and disposed in the support shell 191. The counterweight block 192 is adjacent to the support cover 193 to stand the smart health device 1 upwards. The back plate 112 includes a metal sheet 125 (see FIG. 2). The magnet 194 connects the casing 11 to the support assembly 19 by an attractive force between the magnet 194 and the metal sheet 125.

With the above configuration, the smart health device 1 integrates the body fluid detection module 13, the temperature detection module 14, the electrocardiogram detection module 15, and the blood pressure detection module 16 together. Thus, only a single device is needed to monitor different physiological states or processes of the human body. The user can also communicate with the online doctor or the family member through the video module 18, which allows the online doctor or the family member to fully know the health status of the user.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A smart health device, comprising:
   a casing comprising a side frame and a back plate surrounding edges of the side frame, the side frame defining a first opening, a second opening, a first electrocardiogram area, and a second electrocardiogram area;
   a body fluid detection module disposed in the casing and comprising a detection sheet, the detection sheet disposed in the second opening, the second opening further configured to receive a test paper carrying a body fluid to be tested, the detection sheet configured to detect amounts of biological substances in the body fluid;
   a temperature detection module disposed in the casing and comprising a temperature sensing probe, the temperature sensing probe disposed in the casing and exposed from the first opening, the temperature sensing probe configured to detect a temperature of a human body;
   an electrocardiogram detection module disposed in the casing and comprising at least two electrocardiogram probes, the at least two electrocardiogram probes disposed in the casing and facing the first electrocardiogram area and the second electrocardiogram area, the at least two electrocardiogram probes configured to detect an electrocardiogram of the human body;
   a blood pressure detection module detachably connected to the back plate of the casing, wherein the blood pressure detection module comprises a holding plate, an upper cover, a lower cover, an armband, an air tube, and an air pump assembly, the back plate of the casing is movably connected to the holding plate, the upper cover is connected to the holding plate, the lower cover is connected to the upper cover; the upper cover is disposed between the back plate of the casing and the lower cover, the upper cover and the lower cover cooperatively define a receiving cavity for receiving the air pump assembly and the air tube, the air tube is connected to the air pump assembly and the armband, the air pump assembly is configured to charge or discharge air from the armband, the armband is connected to a surface of the lower cover away from the upper cove and configured to detect a blood pressure of the human body; and
   a control module disposed in the casing and comprising a first control board, the first control board electrically connected to the body fluid detection module, the temperature detection module, the electrocardiogram detection module, and the blood pressure detection module, and configured to obtain the amounts of biological substances, the temperature, the electrocardiogram, and the blood pressure.

2. The smart health device of claim 1, wherein the blood pressure detection module further comprises a second control board, the second control board is received in the receiving cavity and electrically connected to the armband, and configured to obtain the blood pressure.

3. The smart health device of claim 2, further comprising a support assembly detachably connected to the casing, wherein the support assembly comprises a support shell and a counterweight block disposed in the support shell, the counterweight block is configured to stand the smart health device upwards.

4. The smart health device of claim 3, wherein the control module comprises a plurality of conductive terminals exposed from the casing, the upper cover defines a plurality of first through holes, the holding plate defines a plurality of second through holes corresponding to the plurality of first through holes, the second control board comprises a plurality of conductive pins, when the casing is supported by the holding plate, the plurality of conductive pins passes through the plurality of first through holes and the plurality of second through holes and is electrically connected to the plurality of conductive terminals, thereby electrically connecting the second control board and the control module together, the first control board is further configured to obtain the blood pressure from the second control board.

5. The smart health device of claim 4, wherein casing further defines two slots disposed at opposite sides of the plurality of conductive terminals, the holding plate further comprises two protruding blocks disposed at opposite sides of the plurality of second through holes, when the casing is supported by the holding plate, the protruding blocks are received in the slots, thereby positioning the plurality of conductive pins to the plurality of conductive terminals.

6. The smart health device of claim 3, wherein the casing further comprises a metal sheet, the support assembly further comprises a magnet disposed in the support shell, the magnet connects the casing to the support assembly by an attractive force between the magnet and the metal sheet.

7. The smart health device of claim 3, wherein the support assembly further comprises a support cover, a first rubber pad, and a second rubber pad, the first rubber pad and the second rubber pad are respectively disposed at opposite ends of the support shell, the support cover is connected to the first rubber pad and supports the counterweight block.

8. The smart health device of claim 1, wherein the casing further comprises a protrusion, the protrusion is hollow and defines the first opening.

9. The smart health device of claim 1, further comprising a video module, wherein the video module comprises a camera and a microphone, the casing further defines a lens hole and a microphone hole, the camera is disposed in the casing and exposed from the lens hole, the microphone is disposed in the casing and exposed from the microphone hole.

10. The smart health device of claim 1, wherein the blood pressure detection module further comprises a switch, the switch is exposed from the upper cover and electrically connected to the air pump assembly, the switch is configured to control the blood pressure detection module to be on or off.

* * * * *